United States Patent [19]

Glantschnig et al.

[11] Patent Number: 4,726,677
[45] Date of Patent: Feb. 23, 1988

[54] AUTOFOCUSED LIGHTGUIDE PREFORM PROFILER

[75] Inventors: Werner J. Glantschnig, Belle Mead, N.J.; Albert Holliday, Langhorne, Pa.

[73] Assignee: American Telephone and Telegraph Company, AT&T Technologies, Inc., Berkeley Heights, N.J.

[21] Appl. No.: 945,048

[22] Filed: Dec. 22, 1986

[51] Int. Cl.⁴ .................. G01N 21/84; G01N 21/47
[52] U.S. Cl. ................................ 356/73.1; 356/128
[58] Field of Search .............. 356/73.1, 121, 125, 356/126, 128

[56] References Cited

U.S. PATENT DOCUMENTS 3,617,755 11/1971 Arnaud .................. 356/121
4,227,806 10/1980 Watkins ................. 356/73.1
4,515,475 5/1985 Payne et al. ............ 356/73.1

OTHER PUBLICATIONS

"Nondestructive Determination of Refractive Index Profile of an Optical Fiber: Backward Light Scattering Method", Applied Optics, vol. 18, No. 7 (1 Apr. 1979)—C. Saekeang & P. L. Chu.
"How Accurately Can One Reconstruct an Index Profile from Transverse Measurement Data?", W. J. Glantschnig; Jrnl. of Lightwave Tech., vol. LT-3, No. 3, (3 Jun. 1985).

Primary Examiner—Vincent P. McGraw
Attorney, Agent, or Firm—Douglas J. Kirk; Roderick B. Anderson

[57] ABSTRACT

A method for automatically determining the refractive index profile of a lightguide preform.

2 Claims, 7 Drawing Figures

1

AUTOFOCUSED LIGHTGUIDE PREFORM PROFILER

TECHNICAL FIELD

The invention is directed to a method for determining various parameters of a lightguide preform. In particular, the invention is directed to a non-contact, non-destructive technique for measuring the refractive index profile of such a preform.

BACKGROUND OF THE INVENTION

The invention is directed to a method for determining various parameters of a lightguide preform. In particular, the invention is directed to a non-contact, non-destructive technique for measuring the refractive index profile of such a preform. A lightguide preform is comprised of a substantially cylindrical glass core surrounded by a glass cladding which may be fabricated by several processes well known in the art. These processes involve the thermochemical production of glass from appropriate glass precursor vapors.

The refractive index profile of an optical fiber is substantially the same as the profile of the preform from which it was drawn. Therefore, deviations from the refractive index profile n(r) of the preform may result in unacceptable transmission characteristics of the fiber drawn therefrom. Thus, it becomes most advantageous to determine the refractive index profile of the preform prior to drawing fiber therefrom to avoid the expense of producing kilometers of fiber that would be unacceptable for its intended use.

One non-destructive technique for measuring the refractive index of a lightguide preform is described in U.S. Pat. No. 4,227,806 to Watkins which issued on Oct. 14, 1980 and is incorporated by reference herein. In that patent a laser beam scans an optical fiber preform and the deflection angle $\theta$ thereof is measured as the beam exits the preform. The deflection angle $\theta$ is plotted versus the incident beam position and that plot is integrated to provide a curve that is compared to theoretically developed plots for refractive index profiles characterized by known parameters.

The technique developed by Watkins has since been improved in several important respects. Rather than determining certain index profile parameters by comparing the integrated $\theta$-curve to equivalent curves computed for refractive index profiles with known parameters, the index profiles obtained with the improved technique are directly computed from the measured deflection angles $\theta$. If $\theta(x)$ is the angle of refraction observed for a beam incident on the preform a distance x from the preform axis, then the radius of closest approach to the preform axis r(x) of that beam is given by $$r(x) = x \exp\left\{ -\frac{1}{\pi} \int_x^R \frac{\theta(t)\,dt}{\sqrt{t^2 - x^2}} \right\}$$

where R is the preform radius and t is the variable of integration. The refractive index $n[r(x)]$ at radius $r(x)$ is given as $$n(r) = n(R) \exp\left\{ \frac{1}{\pi} \int_x^R \frac{\theta(t)\,dt}{\sqrt{t^2 - x^2}} \right\}$$

where n(R) is the refractive index of the preform at its surface. Using these equations to establish the refractive index profile of an optical fiber preform is preferable to using Watkin's earlier approach since these equations are applicable to a much larger class of index profiles.

While the technique as outlined up to this point has been found to be effective and useful for determining the refractive index profiles of lightguide preforms it has one deficiency. The measurement process requires that an operator manually focus the system prior to scanning the laser beam past the preform. This manual focusing process amounts to an undesirable machine-operator interaction because (a) the quality of an index profile measurement depends at least partially on the skill of the operator affecting the focusing, and (b) without the focusing process the measurement could be totally automated. Clearly, eliminating this manual focusing procedure would be desirable.

SUMMARY OF THE INVENTION

The foregoing problem has been overcome by the instant method of determining the refractive index profile of a lightguide preform by directing a beam of light through a focusing lens to cause said beam to converge towards the focal plane of the lens and then diverge and impinge upon an apparatus to detect deflection angles of the beam and determine the refractive index profile of the preform, comprising the steps of: imparting relative motion between the beam and the preform, the longitudinal axis of the preform being substantially perpendicular to the axis of the beam, until the edge of said preform is detected; imparting relative motion between the beam and the preform until the beam no longer contacts the preform; moving the preform parallel to the axis of the beam until said preform contacts the diverging portion of the beam; moving the preform parallel to the axis of the beam but in the opposite direction until said preform contacts the diverging portion of the beam on the other side of the beam focus while periodically monitoring the deflection angle of the beam; determining the position of the focal plane based upon the deflection angle information; moving the preform axis into the focal plane; and scanning the preform with the beam of light to determine the refractive index profile thereof. All these steps are under computer control. Apart from the initial setup procedure which consists of inserting the preform into the preform tank and adjusting the tilt of its axis such that the preform is suspended precisely vertically, no operator interventions is needed during the measurement thereof.

DETAILED DESCRIPTION

The instant invention is set forth in the context of automatically, nondestructively determining parameters of a graded index lightguide fiber preform. However, such description is for purposes of exposition and not for limitation and preforms having other profiles (e.g., step index) can be characterized using the instant techniques.

Figure 1:
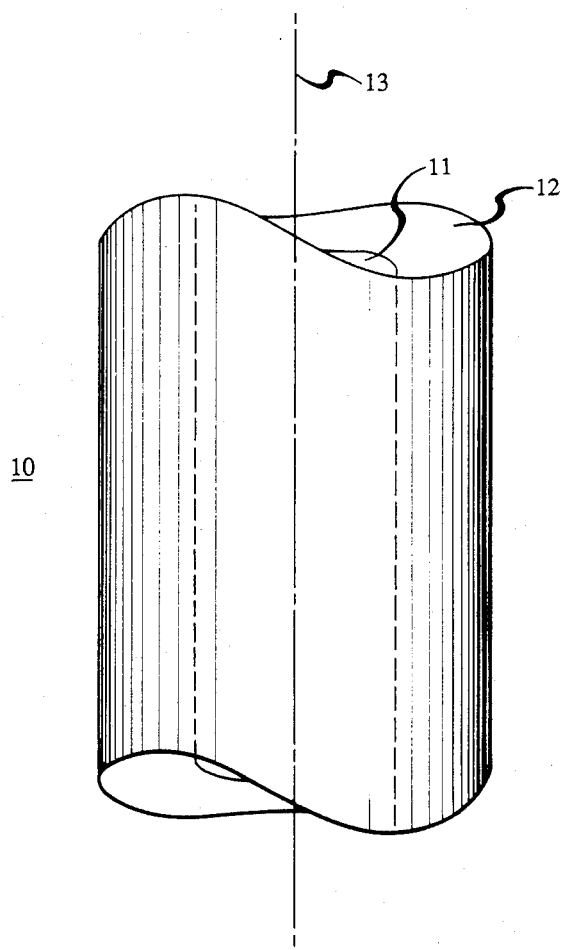
FIG. 1 is a partial sectional view of a lightguide fiber preform.

FIG. 1 depicts a section of a lightguide fiber preform (not to scale), generally designated by the numeral 10, which is comprised of a substantially cylindrical core 11 surrounded by a cladding 12 which may have been fabricated by any of the well known prior art techniques. The core 11 has a slightly higher refractive index than the cladding 12. In the graded index preform 10 of the exemplary embodiment, the refractive index of the core 11 increases toward the axis 13 of the preform resulting in a substantially parabolic refractive index profile n(r).

Figure 2:
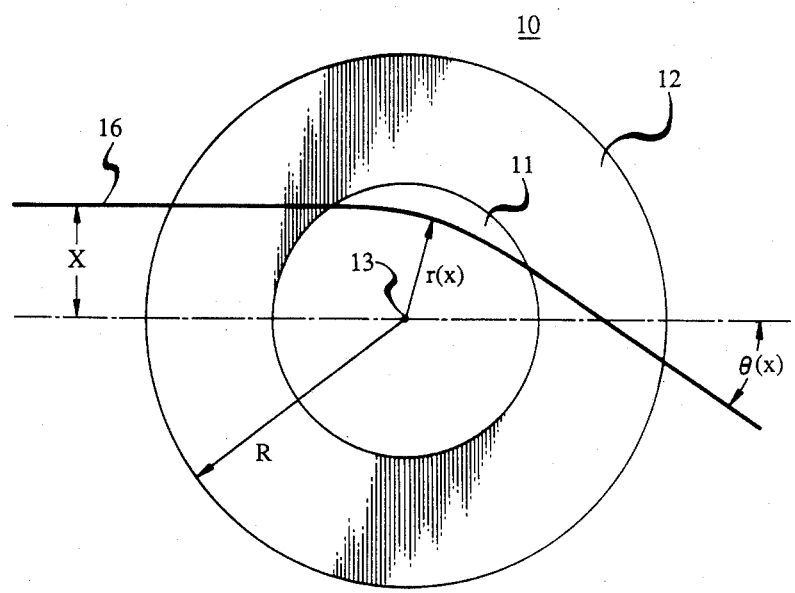
FIG. 2 is an enlarged cross-sectional view of the preform shown in FIG. 1.

FIG. 2 is an enlarged cross-section of the preform 10, shown in FIG. 1, taken in the plane perpendicular to the axis 13 of the preform. A light beam 16 propagating in the plane perpendicular to the preform axis 13 is shown directed toward the preform 10. The preform 10 is assumed to be surrounded by a fluid whose index matches that of the cladding of the preform. As a consequence the beam 16 is not refracted at the surface of the preform 10. However, the beam 16 is being bent inside the core 11 which is assumed to have a graded index such that the index is increasing toward the axis 13 of the preform 10. If the beam 16 is initially incident a distance x from the axis of the preform 10, its distance of closest approach to the preform r(x) is typically smaller than x because of refraction inside the core 11. Upon emerging from the preform 10 the beam appears deflected by an angle $\theta(x)$. The angle $\theta(x)$ is the angle between the direction of the incident beam 16 and that of the emerging beam.

Figure 3:
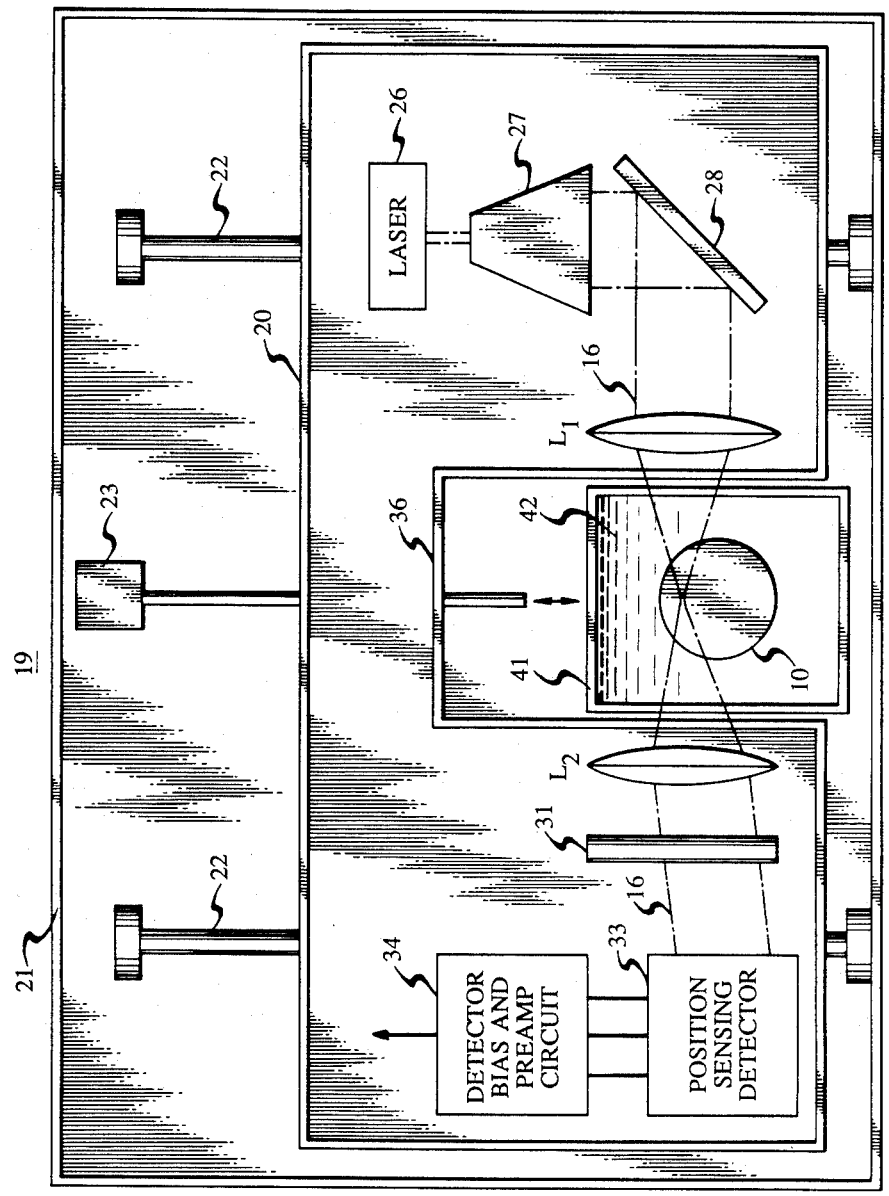
FIG. 3 is a diagrammatic representation of an apparatus in which the instant invention is implemented.

FIG. 3 depicts a preform profiling system 19 in a schematic fashion. The optical components of this system are mounted on a movable platform 20 supported by a baseplate 21. This platform 20 is mounted on rails 22 and driven by a computer controlled stepper motor 23. On the platform 20 are mounted a laser 26 (e.g., HeNe) or any other coherent light source, a beam expander 27, a mirror 28, two lenses $L_1$ and $L_2$, a cylindrical lens 31 and a position-sensing detector 33 with some associated electronics 34. Between lenses $L_1$ and $L_2$ there is a cutout 36 in the platform 20 which accommodates the preform tank 41 which is mounted to the base plate 21. The tank 41 which has transparent glass windows is filled with an oil 42 whose index of refraction closely matches that of the cladding 12 of the preform 10. During a measurement the preform 10 is positioned inside the stationary tank 41 and the laser beam 16 is scanned through the preform 10 by translating the stage on which all optical components are mounted. The purpose of lens $L_1$ is to focus the expanded laser beam 16 down to a spot roughly 20 micrometers in diameter. Lens $L_1$ is positioned such that the focal spot is located in the center of the preform tank 41. The diverging beam 16 is subsequently turned into an expanded parallel beam again by lens $L_2$. This beam 16 is compressed in one dimension only by means of cylindrical lens 31 before it impacts on the detector 33. This detector 33 and lens $L_2$ are spaced precisely a distance $f_2$ apart, where $f_2$ is the focal length of lens $L_2$. Hence, if a beam originally incident a distance x from the preform axis 13 after being refracted impacts on the detector a distance d(x) offset from the center of the detector, the angle of deflection $\theta(x)$ is given as $$\theta(x) = \tan^{-1}\left[\frac{d(x)}{f_2}\right]$$

Figure 4:
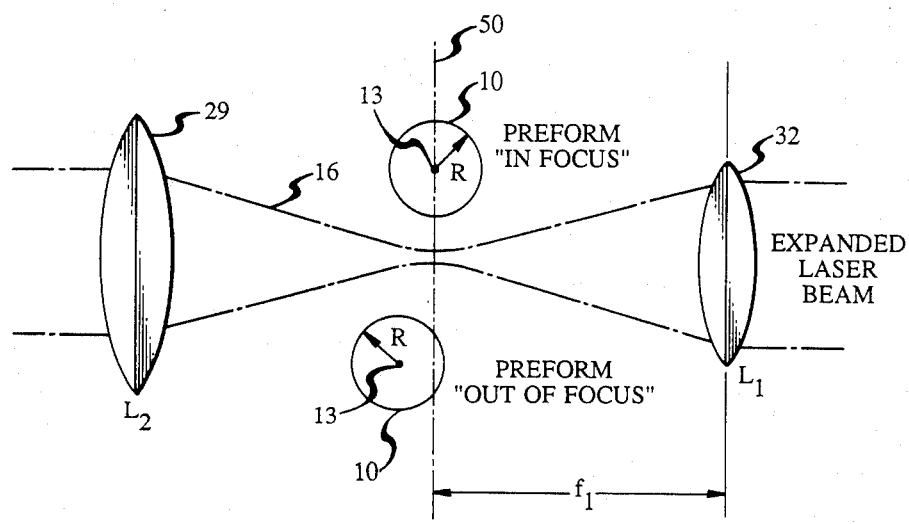
FIG. 4 is a schematic view of preforms that are in and out of the focal plane of a focusing lens.

In order to obtain detailed and accurate information about the structure of the profile of the preform 10 it is necessary to maximize the spatial resolution of the profile by focusing the system before data taking. This process comprises adjusting the position of the preform 10 until its axis lies in the focal plane 50 of the lens $L_1$ located on the laser side of the preform tank 41 as shown in FIG. 4. If the axis of the preform 10 lies in the focal plane 50 of lens $L_1$ the system is considered focused.

It turns out that focusing the system is not as simple a task as it would seem. The laser beam 16 is barely visible inside the preform tank 41 and even it it were, an alignment of the preform axis 13 with the naked eye would not be adequate since even small offsets from the focal plane 50 have a large adverse effect on the spatial resolution of the system. For this reason some hardware aids are usually employed in order to assist the operator with the focusing procedure. In one known technique, the two signal outputs from the linear position sensor 33 are fed into an oscilloscope and their difference, which is proportional to the angle of refraction, is displayed on the CRT as the beam 16 is swept back and forth across the preform 10. At the same time the preform 10 is moved parallel to the beam axis until the oscilloscope trace oscillations are maximized. This will happen when the preform axis 13 lies in the focal plane 50 of the lens $L_1$ in FIG. 4. Accordingly, the operator ultimately decides whether or not the system is adequately focused and, hence, it is subjective.

In order to eliminate this operator dependence, the instant automatic focusing procedure was developed. In terms of additional hardware only one motorized linear stage (not shown) is required, allowing the preform 10 to be moved horizontally, under computer control, parallel to the axis of the beam 16. If this hardware feature is already present, automatic focusing is simply a matter of the use of well known control circuitry or software to move the linear stage.

Before executing the focusing procedure the profiling system 19 must be set up properly. This entails positioning the preform 10 such that it is roughly centered in the preform tank 41 (see FIG. 3) and moving the laser beam 16 outside the preform. The reason for roughly centering the preform 10 in the tank 41 is to ascertain that the axis 13 of the preform 10 is in the vicinity of the focal plane 50 of lens $L_1$ in FIG. 4 prior to starting the autofocusing procedure. It is assumed here that the profiler optics have been set up such that the beam focus is located in the center of the tank 41. This can be done by inserting a 20 micron diameter pinhole into the center of the preform tank 41 and subsequently adjusting the position of lens $L_1$ until the beam 16 is focused through the pinhole.

Figure 5:
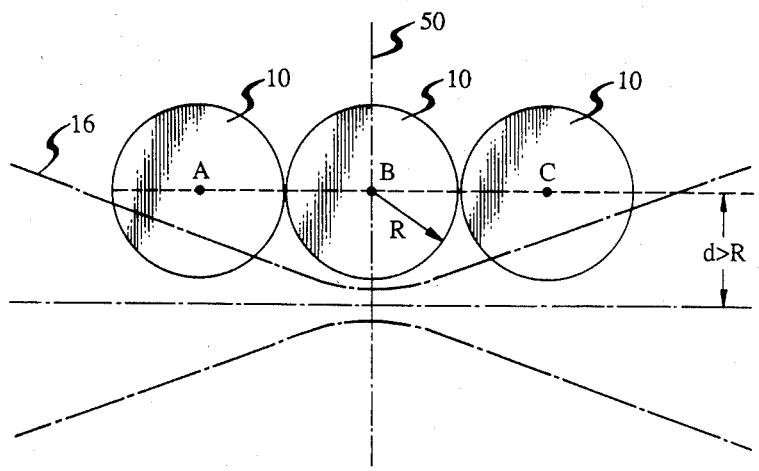
FIG. 5 schematically depicts the movement of a preform relative to a focused beam of light.

There are three steps to autofocusing. First, the laser beam 16 is moved towards the preform 10 until the edge of the preform is detected. It is of absolute necessity that the edge of the preform 10 be reliably detected. For this reason the index matching fluid 42 is intentionally maintained at a temperature such that a refractive index mismatch of about 0.001 between the fluid and the silica cladding 12 is created. The effects of the mismatch are later compensated for using known numerical techniques. Once the edge of the preform 10 is detected, the beam 16 is backed up just enough to position it outside the preform 10 again such that no deflection is being observed. Then the perform 10 is moved parallel to the axis of the beam 16 to the left as shown in FIG. 5. At this point the preform 10 partially intercepts the beam 16 again due to the fact that the beam converges towards and then diverges from the focal plane 50. A preform 10 located at or close to (position B) the focal plane 50 does not intercept the beam 16, but it will do so if moved sufficiently to the left or the right of the focus.

Referring again to FIG. 5, the second step of the autofocusing procedure consists of moving the preform 10 from position A to position C in half mm step increments. After each step a deflection angle reading is taken. As long as the preform 10 intercepts the laser beam 16 to the left of the focal plane 50, a deflection of the beam will be observed. Subsequently, there will be a region, centered about the focus, where the preform 10 will be outside the beam 16 and no refraction will be observed. Finally, as the preform 10 approaches position C it will start to intercept the beam 16 again.

Figure 6:
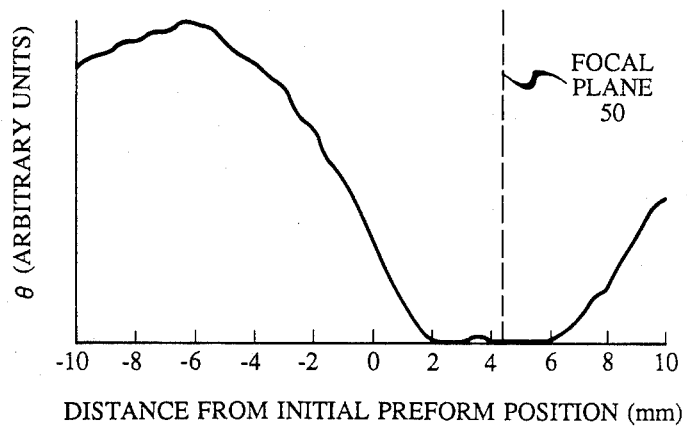
FIGS. 6 and 7 are deflection angle plots of preforms having an axis out and in, respectively, the focal plane of the focusing lens.
Figure 7:
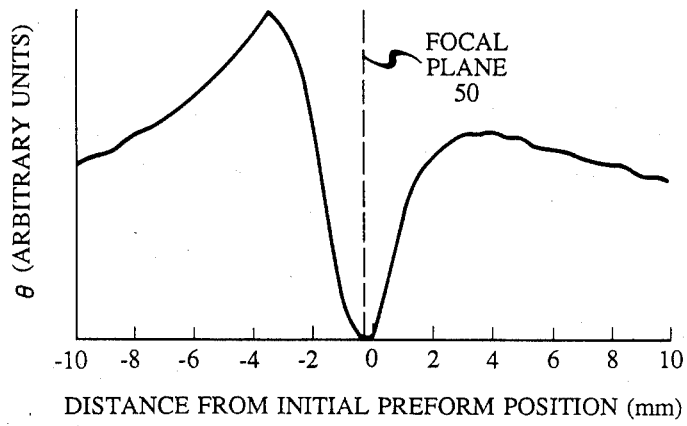

Two actual deflection angle plots obtained during such focusing sweeps are shown in FIGS. 6 and 7. The FIG. 6 plot was obtained for the case in which the preform 10 was initially positioned about 4.5 mm to the left of the focal plane. The FIG. 7 plot is a typical result obtained after the second iteration or if the preform happened to be close to the focus the first time around.

Finally, the last step of the focusing routine consists of moving the preform 10 to the left to the position of the focal plane 50 taken as the center of the zero deflection range obtained during the translation of the preform from position A to position C in FIG. 5. At this point the system is ready for the data taking scan.

It is to be understood that the above-described embodiments are simply illustrative of the principles of the invention. Various other modifications and changes may be devised by those skilled in the art which will embody the principles of the invention and fall within the spirit and scope thereof.

What is claimed is:

1. A method of determining the refractive index profile of a lightguide preform by directing a beam of light through a focusing lens to cause said beam to converge towards the focal plane of the lens and then diverge and impinge upon an apparatus which detects deflection angles of the beam to determine the refractive index profile of the preform, comprising the steps of:

imparting relative motion between the beam and the preform, the longitudinal axis of the preform being substantially perpendicular to the axis of the beam, until the edge of said preform is detected;

imparting relative motion between the beam and the preform until the beam no longer contacts the preform;

moving the preform parallel to the axis of the beam until said preform contacts the beam;

moving the preform parallel to the axis of the beam in the opposite direction until said preform contacts the beam on the opposite side of the focal plane while periodically monitoring the deflection angle of the beam;

determining the position of the focal plane based upon the deflection angle information;

moving the preform axis into the focal plane; and scanning the preform with the beam of light to determine the refractive index profile thereof.

2. Apparatus for automatically determining the refractie index profile of a lightguide preform by directing a beam of light through a focusing lens to cause said beam to converge towards the focal plane of the lens and then diverge and impinge upon an apparatus which detects deflection angles of the beam to determine the refractive index of the preform, comprising:

means for imparting relative motion between the beam and the preform, the longitudinal axis of the preform being substantially perpendicular to the axis of the beam, until the edge of the preform is detected;

means for imparting relative motion between the beam and the preform until the beam no longer contacts the preform;

means for moving the preform parallel to the axis of the beam until said preform contacts the beam;

means for moving the preform parallel to the axis of the beam, in the opposite direction, until said preform contacts the beam, on the opposite side of the focal plane, while periodically monitoring the deflection angle of the beam;

means for determining the position of the focal plane based upon the deflection angle information;

means for moving the preform axis into the focal plane; and means for scanning the preform with the beam of light to determine the refractive index profile thereof.

* * * * *